(12) United States Patent
Kim et al.

(10) Patent No.: US 10,353,226 B2
(45) Date of Patent: Jul. 16, 2019

(54) ELECTROCHEMICAL MIRROR

(71) Applicant: SAMSUNG ELECTRONICS CO., LTD., Suwon-si (KR)

(72) Inventors: Young Soo Kim, Suwon-si (KR); Hyun Ho Lee, Changwon-si (KR); Tae Soon Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 99 days.

(21) Appl. No.: 15/716,715

(22) Filed: Sep. 27, 2017

(65) Prior Publication Data

US 2018/0088362 A1    Mar. 29, 2018

(30) Foreign Application Priority Data

Sep. 27, 2016 (KR) .................. 10-2016-0124028

(51) Int. Cl.
*G02F 1/01* (2006.01)
*G02F 1/061* (2006.01)
*G02F 1/157* (2006.01)
*G02F 1/163* (2006.01)
(Continued)

(52) U.S. Cl.
CPC .............. *G02F 1/061* (2013.01); *B60R 1/088* (2013.01); *C07C 309/66* (2013.01);
(Continued)

(58) Field of Classification Search
CPC . G02F 1/00; G02F 1/01; G02F 1/0102; G02F 1/0107; G02F 1/0121; G02F 1/061; G02F 1/03; G02F 1/07; G02F 1/15; G02F 1/1506; G02F 1/1514; G02F 1/155; G02F 1/157; G02F 1/163; G02F 1/19; G02F 2001/1502; G02F 2001/164; G02B 26/02; G09G 3/38; C07C 309/28; C07C 309/64; C07C 309/66; C07C 309/71; C07D 327/04; C07D 333/06; H01L 51/4246;
(Continued)

(56) References Cited

U.S. PATENT DOCUMENTS

| 4,832,467 A * | 5/1989 | Miyagi | .................. B60R 1/088 |
| | | | 359/265 |
| 5,864,420 A * | 1/1999 | Udaka | .................. G02F 1/1506 |
| | | | 359/270 |

(Continued)

FOREIGN PATENT DOCUMENTS

| JP | 2012118188 A1 | 7/2014 |
| JP | 2013180125 A1 | 1/2016 |
| KR | 101475628 B1 | 12/2014 |

OTHER PUBLICATIONS

International Search Report, issued by International Searching Authority in corresponding International Application No. PCT/KR2017/010226, dated Jan. 8, 2018, (PCT/ISA/210).

*Primary Examiner* — Loha Ben
(74) *Attorney, Agent, or Firm* — Sughrue Mion, PLLC

(57) ABSTRACT

An electrochemical mirror includes a first transparent electrode; a second transparent electrode disposed to be spaced apart from the first transparent electrode; and an electrolyte layer disposed between the first transparent electrode and the second transparent electrode and including an electrolyte solution, the electrolyte solution including a compound having a sulfonate functional group or a derivative compound having the same, as an electrolyte solution additive.

20 Claims, 10 Drawing Sheets

(51) Int. Cl.
  *C07C 309/66* (2006.01)
  *C07D 327/04* (2006.01)
  *G02F 1/1506* (2019.01)
  *G02F 1/1523* (2019.01)
  *B60R 1/08* (2006.01)

(52) U.S. Cl.
  CPC ............ *C07D 327/04* (2013.01); *G02F 1/157* (2013.01); *G02F 1/1525* (2013.01); *G02F 1/0102* (2013.01); *G02F 1/0121* (2013.01); *G02F 1/1506* (2013.01); *G02F 1/163* (2013.01)

(58) Field of Classification Search
  CPC ....... H01L 51/44; H01L 51/441; B60R 1/088; B60R 1/12; B60Q 1/26
  USPC ........ 359/228, 245, 253, 265–275; 345/105; 252/582, 583, 586; 362/494; 257/40
  See application file for complete search history.

(56) References Cited

U.S. PATENT DOCUMENTS

| | | | | |
|---|---|---|---|---|
| 5,923,456 A | * | 7/1999 | Tench | G02F 1/1506 359/265 |
| 6,111,685 A | * | 8/2000 | Tench | G02F 1/1506 359/267 |
| 6,256,135 B1 | * | 7/2001 | Tench | G02F 1/1506 359/265 |
| 6,400,491 B1 | * | 6/2002 | Tench | G02F 1/1506 359/267 |
| 6,522,843 B2 | * | 2/2003 | Yamada | G03G 15/1605 399/302 |
| 6,867,894 B2 | | 3/2005 | Asano et al. | |
| 6,992,808 B2 | * | 1/2006 | Shinozaki | G02F 1/15 359/265 |
| 7,312,914 B2 | * | 12/2007 | Shinozaki | G02F 1/15 359/270 |
| 7,450,292 B1 | * | 11/2008 | Burrell | B60R 1/088 359/270 |
| 7,736,813 B2 | * | 6/2010 | Esmiller | G02F 1/1533 359/265 |
| 9,383,619 B2 | * | 7/2016 | Kim | G02F 1/155 |
| 2009/0280414 A1 | | 11/2009 | Koh et al. | |
| 2010/0039692 A1 | | 2/2010 | Yamada et al. | |
| 2014/0065512 A1 | | 3/2014 | Kwon et al. | |
| 2014/0218781 A1 | | 8/2014 | Kobayashi et al. | |
| 2014/0293508 A1 | | 10/2014 | Jang et al. | |
| 2018/0088428 A1 | * | 3/2018 | Kim | G02F 1/1506 |

* cited by examiner

ELECTROCHEMICAL MIRROR

CROSS-REFERENCE TO RELATED APPLICATION

This application claims priority from Korean Patent Application No. 10-2016-0124028, filed on Sep. 27, 2016 in the Korean Intellectual Property Office, the disclosure of which is incorporated herein by reference in its entirety.

BACKGROUND

1. Field

Apparatuses and methods consistent with exemplary embodiments relate to an electrochemical mirror that is electrochemically switchable.

2. Description of the Related Art

Research has been conducted into switching type mirror displays capable of adjusting reflectance and transmittance by external stimulation.

Reflectance and transmittance of switching type mirrors may be adjusted by an electrical, optical, thermal stimulus, and the like. Among these stimuli, methods of using an electrical stimulus may be classified into solid electrolyte methods using liquid crystals and electrochromic properties and liquid electrolyte methods.

The solid electrolyte methods artificially adjust reflection and/or transmission by applying a relatively high voltage. These methods are relatively expensive and require a complex process such as a laminating process.

The liquid electrolyte methods use electrochemical redox reactions of metal ions to implement a switching mirror.

However, in the related art liquid electrolyte methods, metal deposits formed by a liquid electrolyte solution may have low stability due to chemical dissolution of an electrolyte solution-metal layer interface, short lifespan due to high voltage driving, and may develop cracks in the deposited mirror layer causing non-uniformity.

SUMMARY

The exemplary embodiments may address at least the above problems and/or disadvantages and other disadvantages not described above. Also, the exemplary embodiments are not required to overcome the disadvantages described above, and may not overcome any of the problems described above.

One or more exemplary embodiments provide an electrochemical mirror including a sulfonate functional group and a derivative including the same as an electrolyte solution additive to obtain a uniform mirror layer and high electrochemical cycle stability.

In accordance with an aspect of an exemplary embodiment, an electrochemical mirror includes: a first transparent electrode; a second transparent electrode disposed to be spaced apart from the first transparent electrode; and an electrolyte layer disposed between the first transparent electrode and the second transparent electrode and including an electrolyte solution, the electrolyte solution including a compound having a sulfonate functional group or a derivative compound having the same as an electrolyte solution additive.

The sulfonate compound may have at least one of a cyclic form and a linear form.

The electrochemical mirror may have the sulfonate compound having a cyclic form is represented by Structural Formula 1 below:

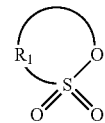

wherein in Structural Formula 1, the $R_1$ group is hydrogen or an alkyl group, an alkene group, or an alkyne group having 1 to 10 carbon atoms.

The alkyl group, alkene group, or alkyne group may include an alkyl group, an alkene group, or an alkyne group, one of hydrogen atoms of which is substituted with the sulfonate compound.

The Structural Formula 1 may include at least one $R_1$ group.

The Structural Formula 1 may include an ether group in at least one of a ring and the $R_1$ group of Structural Formula 1.

The sulfonate compound may include a sulfonate compound in which multiple bonds are formed between carbon molecules.

The sulfonate compound having a linear form may be represented by Structural Formula 2 below:

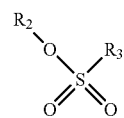

wherein, in Structural Formula 2, the $R_2$ and $R_3$ groups are hydrogen or an alkyl group, an alkene group, or an alkyne group having 1 to 10 carbon atoms respectively.

The alkyl group, alkene group, or alkyne group may include an alkyl group, an alkene group, or an alkyne group, one of hydrogen atoms of which is substituted with the sulfonate compound.

At least one of the $R_2$ and $R_3$ groups of Structural Formula 2 may include an ether group.

The electrolyte solution may include electrodepositable metal salt ions.

The electrodepositable metal salt ions may include at least one selected from the group consisting of silver (Ag), gold (Au), magnesium (Mg), nickel (Ni), bismuth (Bi), chromium (Cr), aluminum (Al) copper (Cu), calcium (Ca), and strontium (Sr).

When a voltage is applied to the transparent electrodes, the electrodepositable ions may be reduced to form an electrochemical mirror layer on the surface of one of the transparent electrodes.

The electrolyte solution may include at least one material selected from an ammonium bromide-based material such as tetra-n-butylammonium bromide (TBABr) and tetra-ethylammonium bromide (TEABr), a halogenated material including a halogenated anion and forming an organic or inorganic ionic salt with the halogenated anion, and tetra-n-butylammonium perchlorate (TBAP).

The electrolyte solution may include at least one solvent selected from the group consisting of water, dimethyl sulfoxide (DMSO), N-methyl-2-pyrrolidone (NMP), acetonitrile (AN), ethylene glycol (EG), γ-butyrolactone (GBL), dimethy formamide (DMF), a glyme-based solvent, an ether-based solvent, a linear or cyclic carbonate-based solvent, and a mixture thereof.

The electrolyte solution may include at least one selected from the group consisting of polyvinyl butyral (PVB), cyano resin, polyvinylidene fluoride (PVDF), polyvinylidene-hexafluoropropylene (PVDF-HFP), and a mixture thereof to improve viscosity and stability of the electrolyte solution.

The first and second transparent electrodes may include electrodes formed on at least one substrate of a glass substrate, a rigid substrate, a polyethylene terephthalate (PET) substrate, and a flexible substrate.

In accordance with an aspect of an exemplary embodiment an electrochemical mirror includes a first transparent electrode disposed on a first substrate; a second transparent electrode which is disposed on a second substrate and faces the first transparent electrode; a first blocking wall and a second blocking wall which connect ends of the first transparent electrode and the second transparent electrode; and an electrolyte layer disposed in a cavity formed between the first transparent electrode, the second transparent electrode, the first blocking wall, and the second blocking wall, the electrolyte layer including an electrolyte solution including electrodepositable metal salt ions and a sulfonate compound, wherein, in response to a voltage being applied to the first transparent electrode and the second transparent electrode, the electrodepositable metal salt ions form an electrochemical mirror layer on a surface of the first transparent electrode and cause the electrochemical mirror to operate in an opaque state, in response to stopping application of the voltage to the first transparent electrode and the second transparent electrode, the electrodepositable metal salt ions become dissociated from the surface of the first transparent electrode and cause the electrochemical mirror to operate in a transparent state, and the sulfonate compound serves as a catalyst accelerating and/or controlling a switching speed between the opaque state and the transparent state, of the electrochemical mirror.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
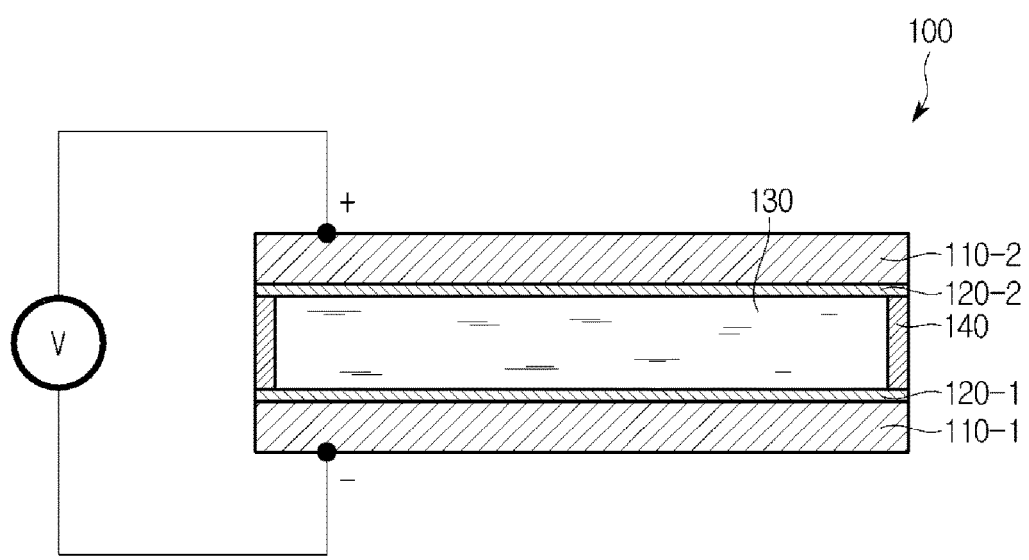
FIG. 1 is a view illustrating a structure of an electrochemical mirror 100 according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It is to be understood that the terms "include" or "have" are intended to indicate the existence of elements disclosed in the specification, and are not intended to preclude the possibility that one or more other elements may exist or may be added.

Throughout the specification, it will be understood that when one element, is referred to as being "on" another element, it can be directly on the other element, or intervening elements may also be present therebetween.

In this specification, terms "first," "second," etc. are used to distinguish one component from other components and, therefore, the components are not limited by the terms.

An expression used in the singular encompasses the expression of the plural, unless it has a clearly different meaning in the context.

Exemplary embodiments relate to a rapidly switchable electrochemical mirror device having electrochemical stability (anti-peeling effect).

An electrochemical mirror device according to exemplary embodiments may include transparent electrodes and an electrolyte layer interposed between the transparent electrodes. The electrochemical mirror device may operate in a light-transmitting mode when no voltage is applied thereto and operate in a light-reflecting mode when a voltage is applied thereto. This is based on redox reactions of an electrolyte solution occurring depending on whether the voltage is applied or not. According to exemplary embodiments, an electrochemical mirror device having high electrochemical stability and excellent cycle characteristics may be provided by adjusting types and amounts of the additives contained in the electrolyte solution.

The electrochemical mirror according to exemplary embodiments has excellent electrochemical stability and cycle characteristics, and may control transmittance by adjusting an applied voltage. Thus, exemplary embodiments may be applied to the field of smart windows and the like to achieve effects of adjusting internal temperature in a building by sunlight entering the building. Application examples of the electrochemical mirror according to exemplary embodiments are not limited thereto, and the electrochemical mirror may also be applied to various other fields.

Figure 2:
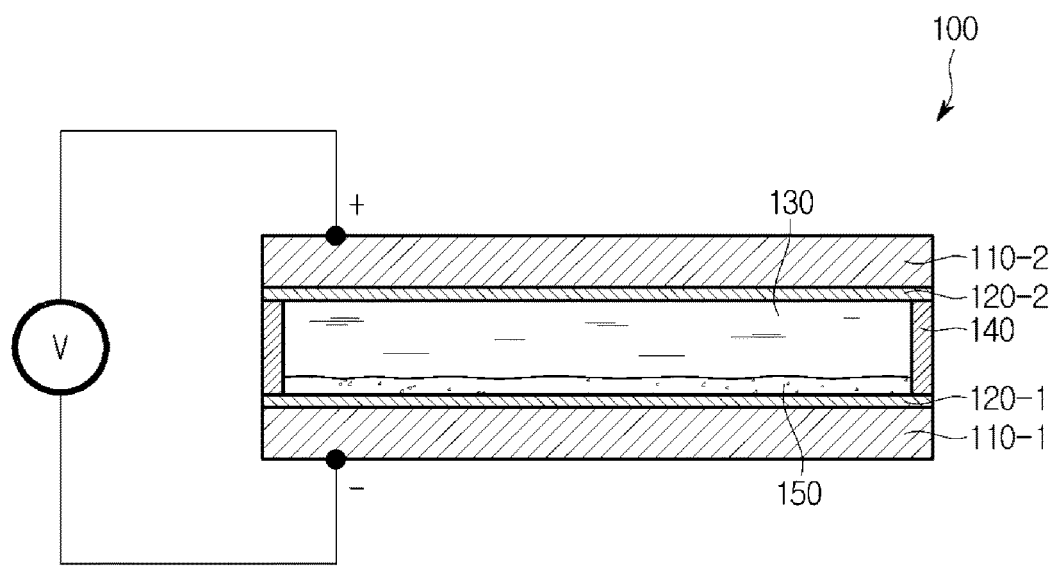
FIG. 2 is a view illustrating an electrochemical mirror 100 when a voltage is applied to the electrodes.

Referring to FIGS. 1 and 2, the electrochemical mirror 100 according to an exemplary embodiment may have a structure in which an electrolyte solution is disposed between transparent electrodes 120-1 and 120-2 facing each other. In more detail, the electrochemical mirror 100 includes a first substrate 110-1, a second substrate 110-2 disposed to be spaced apart from the first substrate 110-1, a first transparent electrode 120-1 disposed on the first substrate 110-1, a second transparent electrode 120-2 disposed on the second substrate 110-2, and an electrolyte layer 130 disposed between the first transparent electrode 120-1 and the second transparent electrode 120-2. According to an exemplary embodiment, one or more blocking walls 140, e.g., first and second blocking walls, may be disposed between the first substrate 110-1 and the second substrate 110-2 to form a cell including a cavity.

The first substrate 110-1 and the second substrate 110-2 may be transparent substrates. For example, the first substrate 110-1 and the second substrate 110-2 may be formed of at least one of a glass substrate, a rigid substrate, a polyethylene terephthalate (PET) substrate, and a flexible substrate.

The first transparent electrode 120-1 and the second transparent electrode 120-2 are transparent electrodes for an electrochemical mirror. Hereinafter, the first transparent electrode 120-1 is defined as a cathode or a working electrode, and the second transparent electrode 120-2 is defined as an anode or a counter electrode. These definitions are merely for the descriptive convenience and the first transparent electrode 120-1 may also serve as an anode and the second transparent electrode 120-2 may also serve as a cathode in accordance with a voltage application method.

The first transparent electrode 120-1 and the second transparent electrode 120-2 may be formed of at least one material selected from indium tin oxide (ITO) fluorine-doped tin oxide (FTO), and indium zinc oxide (IZO). However, the material of the first transparent electrode 120-1 and the second transparent electrode 120-2 is not limited thereto and a laminated structure of conductive transparent electrodes may be provided via coating and doping of an organic material, an inorganic material, and a composite of organic and inorganic materials.

Each of the first transparent electrode 120-1 and the second transparent electrode 120-2 may have a thickness of several hundred nanometers to several hundred micrometers.

The electrolyte layer 130 may be formed of an electrolyte solution, and the electrolyte solution may include an electrodepositable metal salt, an electrolyte, a solvent, a polymer, and an additive.

The electrodepositable metal salt may include at least one among a first metal of a first metal group and a second metal of a second metal group. The first metal of the first metal group may include at least one among silver (Ag), gold (Au), magnesium (Mg), nickel (Ni), bismuth (Bi), chromium (Cr), aluminum (Al), and the like. The second metal of the second metal group may include at least one among copper (Cu), calcium (Ca), strontium (Sr), and the like. The examples of the electrodepositable metal salts are not limited thereto.

Metals of the second metal group may serve as catalysts for promoting nucleation and growth of metals of the first metal group and may form an electrical alloy layer with the metals of the first metal group.

The metals of the second metal group such as copper (Cu), calcium (Ca), and strontium (Sr) may be added within 50% of the metals of the second metal group such as silver (Ag), gold (Au), magnesium (Mg), nickel (Ni), bismuth (Bi), chromium (Cr), and aluminum (Al) for formation of an electrochemical mirror layer 150 of a certain level as illustrated in FIG. 2. However, the content ratio of these metals is not limited to the above-described example.

Hereinafter, exemplary embodiments are described with reference to an electrolyte solution including silver (Ag) and copper (Cu) for convenience. Silver (Ag) and copper (Cu) may be provided in a state dissolved in the electrolyte solution together with salts including nitrate, halide, lactate, sulfide, permanganate, perhalide, and the like. However, these salts are merely examples of forms in which silver and copper are provided and may include any other salts obvious to one of ordinary skill in the art.

Silver (Ag) is a material involved in formation of the electrochemical mirror layer 150. When a voltage from a power source is applied to the first and second transparent electrodes 120-1 and 120-2 of the electrochemical mirror 100, Ag ions (Ag$^+$) contained in the electrolyte solution are reduced on the surface of the first transparent electrode 120-1, which is a cathode, to form the electrochemical mirror layer 150. When the electrochemical mirror layer 150 is formed, the electrochemical mirror 100 may operate in a mirror mode (opaque mode).

Copper (Cu) that serves as a catalyst for nucleation and growth of Ag ions (Ag$^+$) might not be included in the electrolyte solution in accordance with an amount of a compound including a sulfonate functional group.

The electrolyte may include a halogenated material or a pseudohalogenated material. Anions contained in the halogenated material or pseudohalogenated material serve to increase solubility of electrodepositable metal ions included in the electrolyte solution.

Types of halides or pseudohalides may include an ammonium bromide-based material such as tetra-n-butylammonium bromide (TBABr) and tetra-ethylammonium bromide (TEABr), a halogenated material including a halogenated anion and forming an organic or inorganic ionic salt with the halogenated anion, tetra-n-butylammonium perchlorate) (TBAP), and the like. However, the types of available halides or pseudohalides are not limited thereto, and fluorinated materials, chlorinated materials, and iodine-based materials may also be used according to exemplary embodiments.

The solvent serves to dissolve the electrodepositable metal and the electrolyte. The solvent may include at least one solvent selected from the group consisting of water, dimethyl sulfoxide (DMSO), N-methyl-2-pyrrolidone (NMP), acetonitrile (AN), ethylene glycol (EG), γ-butyrolactone (GBL), dimethyl formamide (DMF), a glyme-based solvent, an ether-based solvent, a linear carbonate-based solvent, circular carbonate-based solvent, and any mixture thereof.

The glyme-based solvent may include at least one selected from the group consisting of 1,2-dimethoxy ethane, dimethyl ether (DME), diethylene glycol dimethyl ether (DEGDME), triethylene glycol dimethyl ether (TriEGDME), tetraethylene glycol methyl ether (TEGDME), and any mixture thereof. However, types of available glyme-based solvents are not limited thereto.

The ether-based solvent is a solvent in which an alkylene group, a cycloalkylene group, or an arylene group are connected via an ether group and may include, but is not limited to, at least one of diethyl glycol dimethyl ether, triethylene glycol dimethyl ether, tetraethylene glycol dimethyl ether, and any mixture thereof.

The carbonate-based solvent may include, but is not limited to, at least one of ethylene carbonate (EC), propylene carbonate (PC), dimethyl carbonate (DMC), diethyl carbonate (DEC), and ethyl-methyl carbonate (EMC).

The polymer may be polyvinyl butyral (PVB). The polymer may interact with at least one of the salts and solvents described above. Such interaction may be intermolecular force, van der Waals force, electrostatic interaction, or any combination thereof.

The additive is a material added to the electrolyte solution to increase a switching speed of the electrochemical mirror 100 and may include a compound having a sulfonate functional group or a derivative compound including the same. Hereinafter, the compound having a sulfonate functional group and a derivative compound including the same will be referred to as a sulfonate compound for descriptive convenience.

The additive may also interact with at least one of the salts and solvents described above in the same manner as the polymer. The interaction may be intermolecular force, van der Waals force, electrostatic interaction, or any combination thereof.

The sulfonate compound may be contained in an amount of 0.1 to 10% by weight, preferably 0.1 to 5% by weight, and more preferably 0.1 to 3% by weight, based on a total weight of the electrolyte solution.

When the sulfonate compound is contained in an amount less than 0.1% by weight based on the total weight of the electrolyte solution, it may be difficult to achieve the object of increasing the switching speed of the electrochemical mirror 100. On the contrary, when the amount of the sulfonate compound is too high, the electrolyte solution may react with the blocking walls 140 constituting the cell resulting in destroy of the structure of the cell. Thus, the sulfonate compound may be contained in an appropriate amount in accordance with desired performance of the electrochemical mirror 100.

At least one type of a cycle form or a linear form may be used as the sulfonate compound.

Particularly, a cyclic sulfonate compound may be a propanesultone compound or a butanesultone compound. 1,3-propanesultone may be used as the propanesultone compound and 1,4-butanesultone may be used as the butanesultone compound. However, examples of the propanesultone compound and the butanesultone compound are not limited thereto and may also include modifications.

The cyclic sulfonate compound may be represented by Structural Formula 1 below.

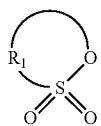

Structural Formula 1

In Structural Formula 1, the $R_1$ group is hydrogen or an alkyl group, an alkene group, or an alkyne group having 1 to 10 carbon atoms.

Alkyl refers to fully saturated branched or unbranched hydrocarbons. At least one hydrogen atom of the alkyl group having 1 to 10 carbon atoms may be substituted with a sulfonate functional group, a halogen atom, a C1-C10 alkyl group substituted with a halogen atom (e.g., $CCF_3$, $CHCF_2$, $CH_2F$, and $CCL_3$), a C1-C10 alkoxy group, a C2-C10 alkoxyalkyl group, a hydroxyl group, a nitro group, a cyano group, an amino group, an amidino group, hydrazine, hydrazone, a carboxyl group or a salt thereof, a sulfonyl group, a sulfamoyl group, a sulfonic acid group or a salt thereof, a phosphoric acid group or a salt thereof, a C1-C10 alkyl group, a C2-C10 alkenyl group, a C2-C10 alkynyl group, a C1-C10 heteroalkyl group, a C1-C10 aryl group, a C6-C10 arylalkyl group, a C6-C10 heteroaryl group, a C7-C10 heteroarylalkyl group, a C6-C10 heteroaryloxy group, a C6-C10 heteroaryloxyalkyl group, or a C6-C10 heteroarylalkyl group.

The halogen atom refers to fluorine, bromine, chlorine, iodine, and the like.

Alkene refers to branched or unbranched hydrocarbons having at least one carbon-carbon double bond. Examples of the alkene may include, but are not limited to, vinyl, allyl, butenyl, isopropenyl, and isobutenyl and at least one hydrogen atom of the alkene group may be substituted with the same substituent described above with reference to the alkyl group.

Alkyne refers to branched or unbranched hydrocarbons having at least one carbon-carbon triple bond. Examples of the alkyne may include, but are not limited to, ethynyl, butynyl, isobutynul, and isopropynyl.

At least one hydrogen atom of the alkyne may be substituted with the same substituents described above with reference to the alkyl group.

Structural Formula 1 may include at least one $R_1$ group. In other words, one $R_1$ group may be bonded to a carbon ring of Structural Formula 1 and two or more $R_1$ groups may be used according to exemplary embodiments.

At least one of the $R_1$ group and a ring of Structural Formula 1 may include an ether group. The cyclic sulfonate compound may have multiple bonds formed between carbon molecules contained in the sulfonate compound. Particularly, the cyclic sulfonate compound may have a double or triple bond formed between carbon molecules.

The linear sulfonate compound may be represented by Structural Formula 2 below.

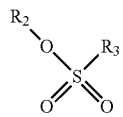

Structural Formula 2

In Structural Formula 2, the $R_2$ and $R_3$ groups are each independently hydrogen or an alkyl group, alkene group, or alkyne group having 1 to 10 carbon atoms.

At least one hydrogen atom of the alkyl group, an alkene group, or an alkyne group may be substituted with the same substituents as those described above with reference to the alkyl group of Structural Formula 1.

At least one of the $R_2$ and $R_3$ groups may have an ether group.

The electrochemical mirror 100 may include a spacer to arrange the first substrate 110-1 and the second substrate 110-2 to be spaced apart from each other and to maintain a cell interval and may further include blocking walls 140 to form the cell. The spacer may be formed of an insulating material such as silicon dioxide ($SiO_2$), but types of spacer material are not limited thereto. The electrolyte solution may be contained in the cell formed by the blocking walls 140. The blocking walls 140 may be formed of a chemical-resistant bonding tape or an ultra-violet (UV)-curable or thermosetting sealant. However, types of the material used to form the blocking wall 140 are not limited thereto.

The electrochemical mirror 100 may have various structures in addition to the structure shown in FIG. 1. For example, the electrochemical mirror 100 may be provided in the form of a switchable electrochemical mirror of a transistor-type or any other appropriate type.

Hereinafter, a method of converting a state of the electrochemical mirror 100 between an opaque state and a transparent state in accordance with whether or not a voltage is applied thereto are described below in detail with reference to FIGS. 1 and 2.

FIG. 1 illustrates a case in which no voltage is applied to the electrochemical mirror 100. When no voltage is applied to the electrochemical mirror 100, the first transparent electrode 120-1, the aligned second transparent electrode 120-2, and the electrolyte layer 130 have high transmittance of light incident on the electrochemical mirror 100. As a result, the electrochemical mirror 100 operates in a transmission mode.

FIG. 2 illustrates a case in which a voltage is applied to the electrochemical mirror 100. As illustrated in FIG. 2, when a voltage is applied to the electrochemical mirror 100, electrochemical reactions occur on the first transparent electrode 120-1, which is a cathode. In other words, Ag ions ($Ag^+$) are reduced to form the electrochemical mirror layer 150 on the surface of the cathode.

A process of forming the electrochemical mirror layer 150 is described in more detail below.

First, when a voltage is applied to the first transparent electrode 120-1 and the second transparent electrode 120-2, copper ions ($Cu2^{30}$) are reduced on the surface of the first transparent electrode 120-1 that is a cathode. Copper reduced on the surface of the cathode serves as a catalyst to aid the growth of Ag ions ($Ag^+$) on the surface of the cathode. As copper grows on the surface of the cathode, reduction of Ag ions ($Ag^+$) is initiated on the surface of the cathode.

On the surface of the cathode, silver grows from initially reduced silver particles while being reduced. Halogen materials (e.g., bromine ions of TBABr) are added to the electrolyte solution as described above. When an electric field is not continuously applied between the first transparent electrode 120-1 and the second transparent electrode 120-2, silver particles reduced on the surface of the cathode are re-oxidized in the form of silver bromide ($AgBr_n^{1-n}$).

Thus, dissociation of Ag ions ($Ag^+$) from the surface of the cathode should be inhibited to form the electrochemical mirror layer 150 by continuously growing silver particles. To this end, the electrochemical mirror layer 150 may be formed on the surface of the cathode by continuously applying a uniform voltage form a power supply between the first transparent electrode 120-1 and the second transparent electrode 120-2.

The electrochemical mirror 100 may be converted into the transparent state again by blocking the voltage being applied between the first transparent electrode 120-1 and the second transparent electrode 120-2, i.e., turning the voltage supply from the power source off.

The electrolyte solution of the electrochemical mirror 100 according to an exemplary embodiment includes a sulfonate compound and a switching speed between a mirror state and a transparent state may be increased by the sulfonate compound. The sulfonate compound serves as a catalyst promoting redox reactions of silver similarly to copper as described above, and thus the electrochemical mirror 100 having a high switching speed may be provided.

Figure 3:
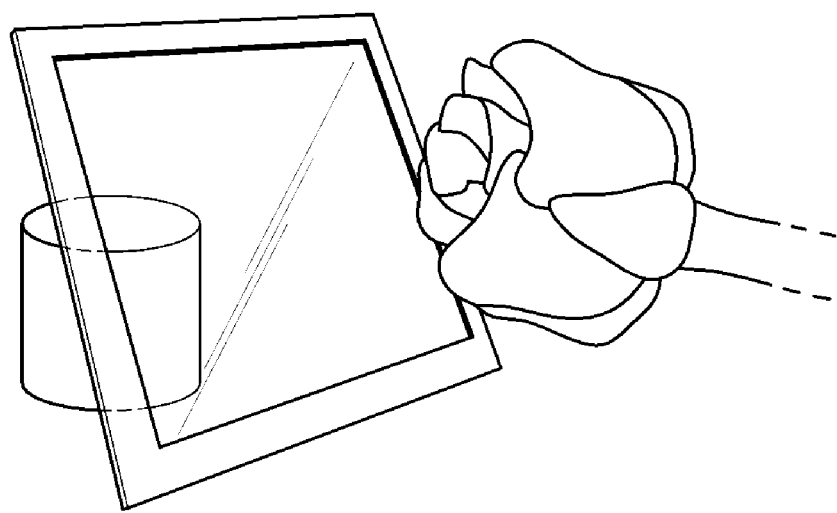
FIG. 3 illustrates the electrochemical mirror 100 operating in the transparent mode.
Figure 4:
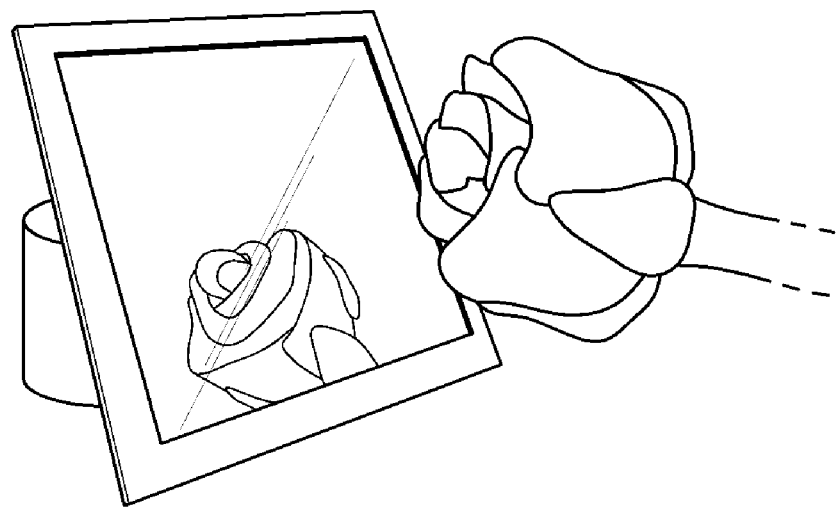
FIG. 4 illustrates the electrochemical mirror 100 operating in the mirror mode.

FIGS. 3 and 4 are views illustrating the electrochemical mirror 100 operating in a transparent mode and a mirror mode, respectively.

When the electrochemical mirror 100 operates in the transparent mode as illustrated in FIG. 3, an object disposed behind the electrochemical mirror 100 may be identified. On the contrary, when the electrochemical mirror 100 operates in the mirror mode as illustrated in FIG. 4, the object disposed behind the electrochemical mirror 100 is not visible and a mirror image of an object disposed in front of the electrochemical mirror 100 may be identified.

Next, test results of physical properties according to exemplary embodiments are described in detail below according to examples and comparative examples.

EXAMPLE 1

5% by weight of PVB and 0.5% by weight of 1,3-propanesultone were added to a solution prepared by dissolving 50 mM of silver nitrate ($AgNO_3$), 10 mM of copper (II) chloride ($CuCl_2$), and 250 mM of tetrabutylammonium bromide (TBABr) in a DMSO solvent based on a total weight of the solution.

EXAMPLE 2

5% by weight of PVB and 1% by weight of 1,3-propanesultone were added to a solution prepared by dissolving 50 mM of $AgNO_3$, 10 mM of $CuCl_2$, and 250 mM of TBABr in a DMSO solvent based on a total weight of the solution.

EXAMPLE 3

5% by weight of PVB and 1% by weight of 1,4-butanediol dimethanesulfonate were added to a solution prepared by dissolving 50 mM of $AgNO_3$, 10 mM of copper (II) chloride ($CuCl_2$), and 250 mM of TBABr in a DMSO solvent based on a total weight of the solution.

COMPARATIVE EXAMPLE 1

5% by weight of PVB was added to a solution prepared by dissolving 50 mM of $AgNO_3$, 10 mM of $CuCl_2$, and 250 mM of TBABr in a DMSO solvent based on a total weight of the solution, and the mixed solution was used as an electrolyte solution of Comparative Example 1.

Physical properties of the electrolyte solutions prepared according to Examples 1, 2, and 3 and Comparative Example 1 were measured by using the following methods.

Electrochemical Impedance Spectroscopy (EIS)

Interfacial resistance of cells against the electrolyte solutions according to Example 1, Example 2, and Comparative Example 1 was measured in a frequency range of 500 mHz to 200 kHz in a −3 V mirroring state.

Switching Speed

A switching time from a transparent mode to a mirror mode (hereinafter, referred to as mirroring time) and a switching time from the mirror mode to the transparent mode (hereinafter, referred to as transparentizing time) of each of the electrolyte solutions prepared according to Example 1, Example 2, and Comparative Example 1 were measured. Mirroring time and transparentizing time were measured more than 5 times respectively and maximum and minimum values were excluded to secure the reliability.

Cyclic Voltammogram (CV)

Electrochemical redox behavior of the electrolyte solutions according to Examples 1, 2, and 3 and Comparative Example 1 were measured under the conditions of 20 mV/sec, a voltage of −3 V to 1 V, and 100 cycles. CV measurement was performed for stabilization of transparent electrode cells after 10 redox cycles.

Experimental results are described in detail below.

Figure 5:
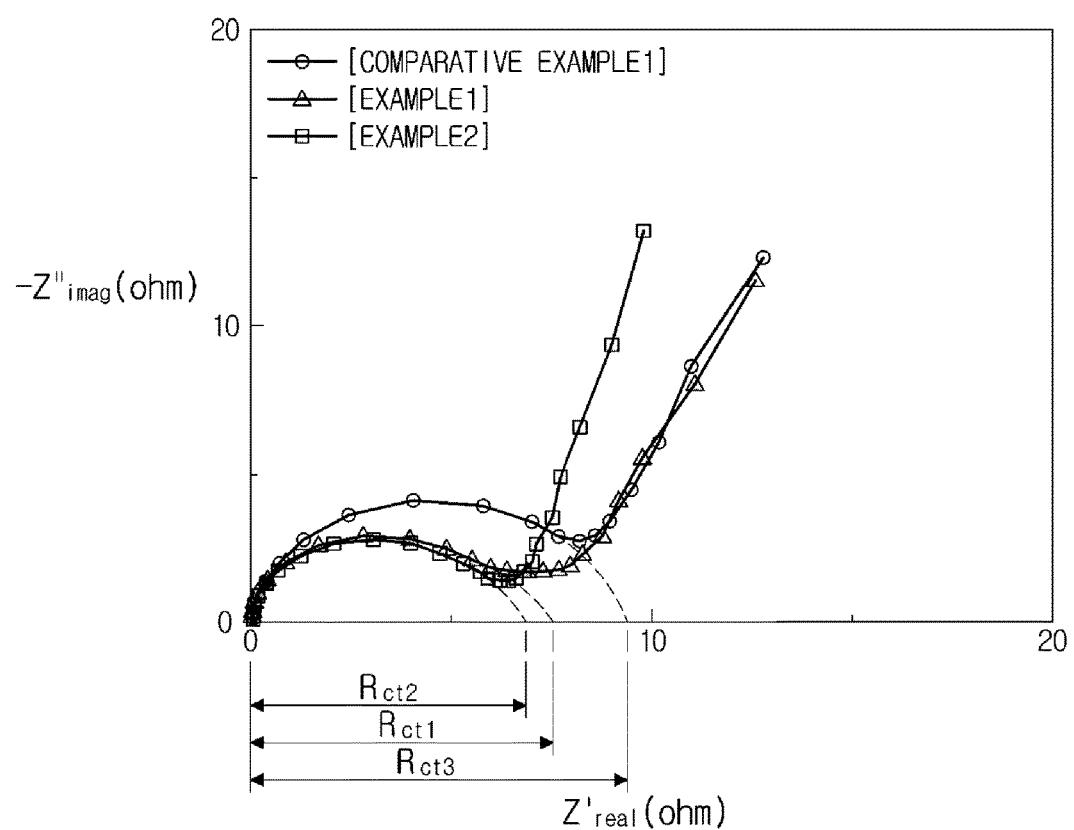
FIG. 5 is a graph illustrating results of electrochemical impedance spectroscopy (EIS) measurement.

FIG. 5 is a graph illustrating results of electrochemical impedance spectroscopy (EIS) measurement. FIG. 5 illustrates interfacial resistance of the cell against each of the electrolyte solutions according to Example 1, Example 2, and Comparative Example 1. Solution resistance was arbitrarily removed and only differences in interfacial resistance were compared. Regarding interpretation of the graph, a diameter of a semi-circle shown the horizontal axis of the graph indicates interfacial resistance of the electrolyte solution.

Based on the test results, it was confirmed that interfacial resistances Rct1 and Rct2 of the electrolyte solutions according to Examples 1 and 2 including 1,3-propanesultone additive were lower than an interfacial resistance Rct3 of the electrolyte solution according to Comparative Example 1 which did not include 1,3-propanesultone additive.

Particularly, the interfacial resistance of the electrolyte solution according to Example 2 including a higher amount of 1,3-propanesultone additive was lower than the interfacial resistance of the electrolyte solution according to Example 1. Accordingly, it was confirmed that better mirror characteristics may be achieved as the amount of the 1,3-propanesultone additive increases.

Figure 6:
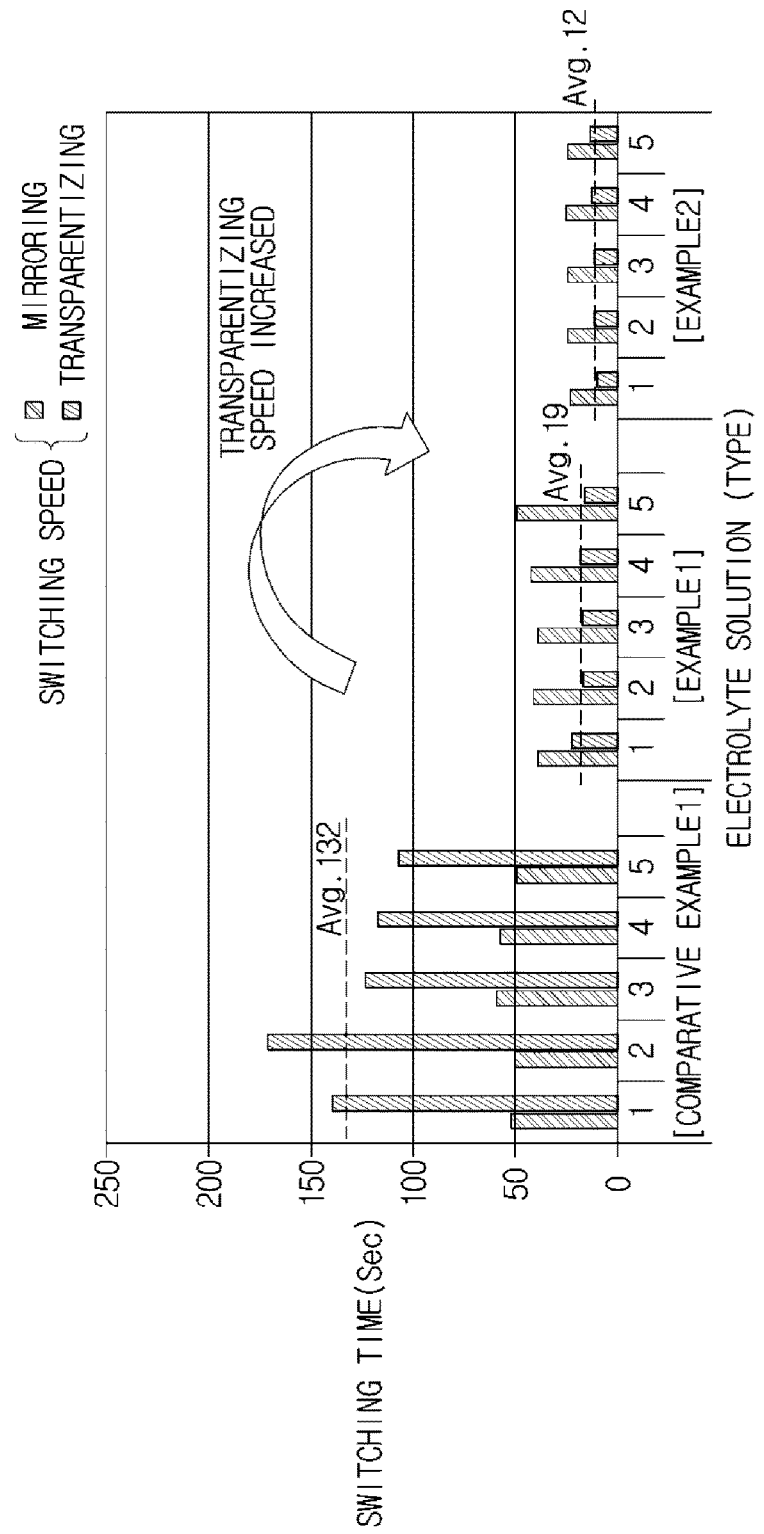
FIG. 6 is a graph illustrating switching speeds of the electrolyte solutions prepared according to Examples 1, 2, and 3.

FIG. 6 is a graph illustrating switching speeds of the electrolyte solutions prepared according to Examples 1, 2, and 3. The horizontal axis of FIG. 6 indicates types of the electrolyte solution according to Examples 1, 2, and 3 and the vertical axis indicates switching time (switching speed).

Upon comparison of mirroring speeds and transparentizing speeds of the electrolyte solutions according to Examples 1 and 2 with those of the electrolyte solution according to Comparative Example 1, it was confirmed that the electrolyte solutions according to Examples 1 and 2 including the 1,3-propanesultone additive had higher mirroring speeds and transparentizing speeds than those of the electrolyte solution according to Comparative Example 1 which did not include the 1,3-propanesultone additive.

Upon comparison of mirroring speeds of the electrolyte solutions according to Examples 1 and 2 and Comparative Example 1 with transparentizing speeds thereof, first, it was confirmed that the electrolyte solution according to Comparative Example 1 had a lower transparentizing speed compared to a mirroring speed. It was confirmed that the electrolyte solutions according to Examples 1 and 2 had higher transparentizing speeds than mirroring speeds.

Accordingly, it was confirmed that both of the mirroring speed and the transparentizing speed increase by adding the 1,3-propanesultone additive to the electrolyte solution. Particularly, upon comparison of the transparentizing speed of Example 2 with that of Comparative Example 1, it was confirmed that the transparentizing speed according to Example 2 was higher than that of the electrolyte solution according to Comparative Example 1 by about 11 times.

Upon comparison of switching speeds of the electrolyte solutions in Examples 1 and 2, it was confirmed that both of the mirroring speed and the transparentizing speed increased in the electrolyte solution according to Example 2 including a high content of the 1,3-propanesultone additive in comparison with Example 1. Thus, it was confirmed that the switching speed increases as the content of the 1,3-propanesultone additive increases.

Figure 7:
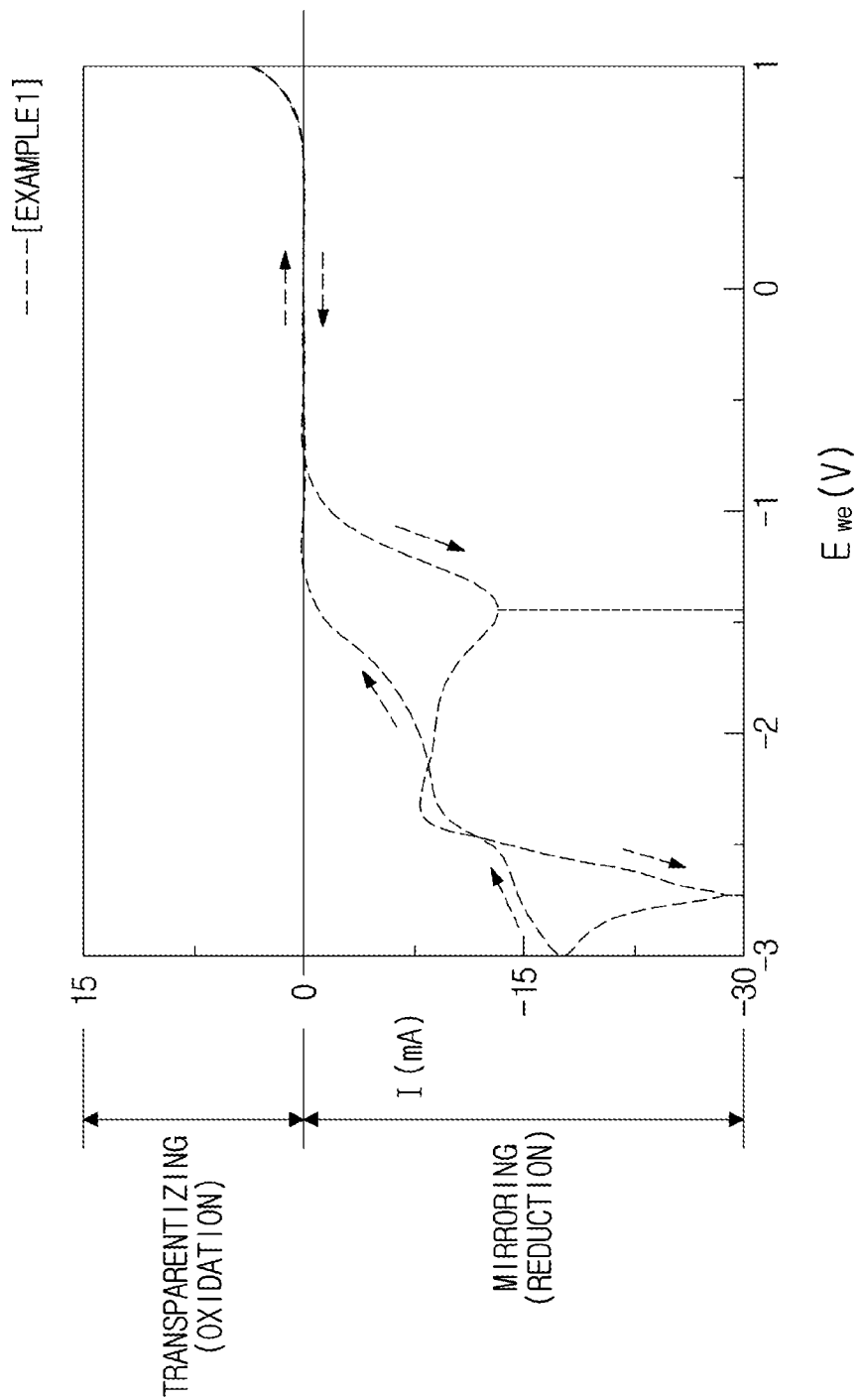
FIG. 7 illustrates CV curves of the electrolyte solution according to Example 1.
Figure 8:
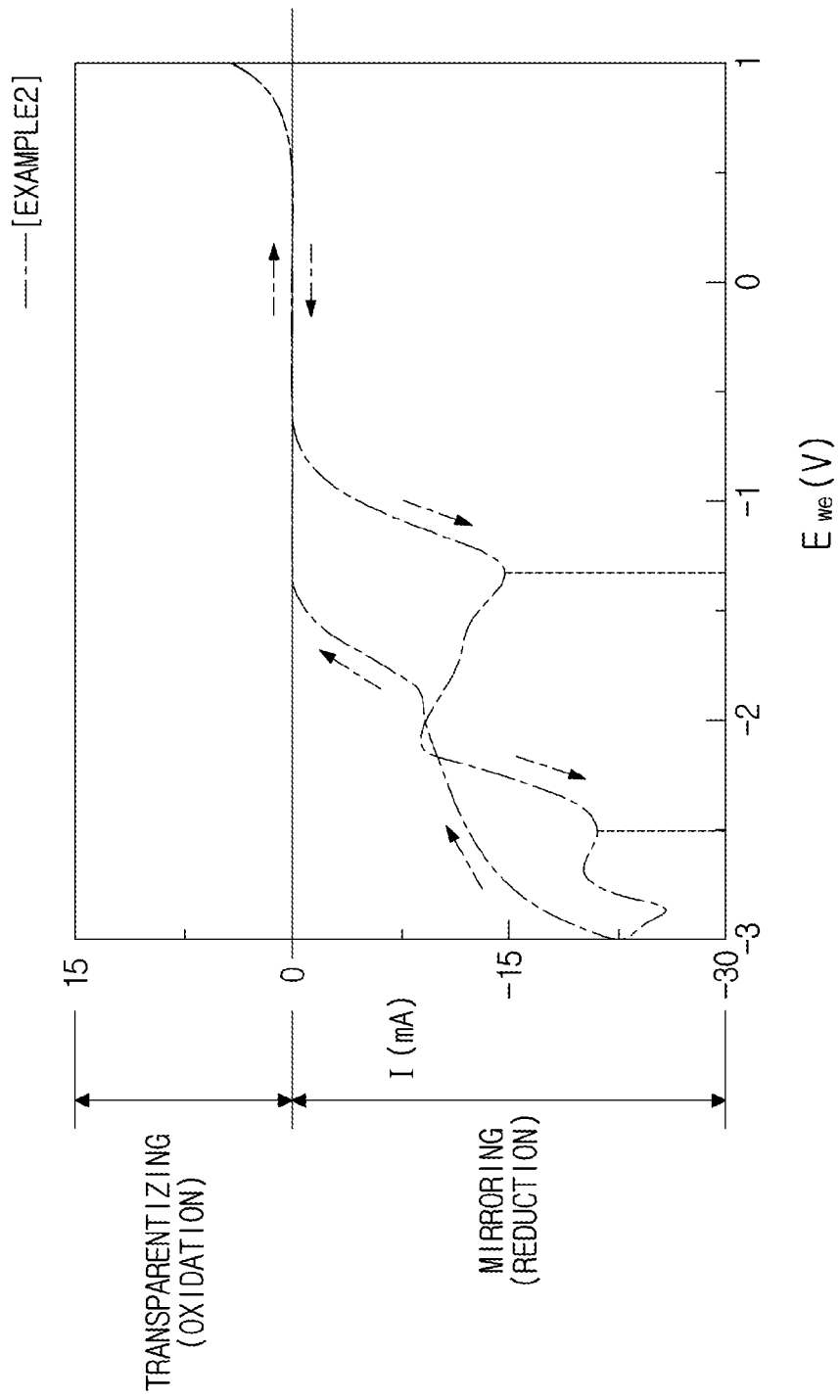
FIG. 8 illustrates CV curves of the electrolyte solution according to Example 2.
Figure 9:
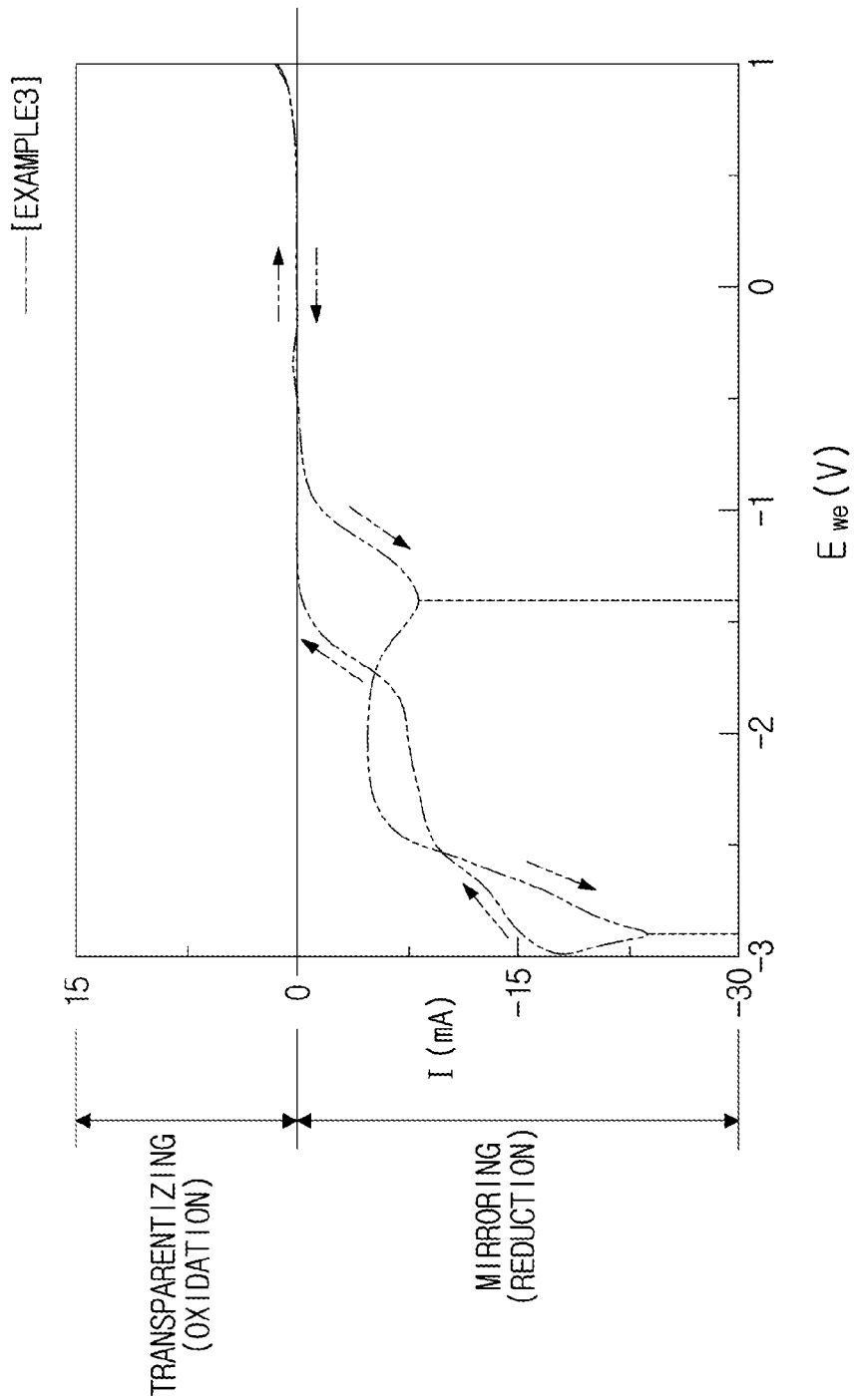
FIG. 9 illustrates CV curves of the electrolyte solution according to Example 3.
Figure 10:
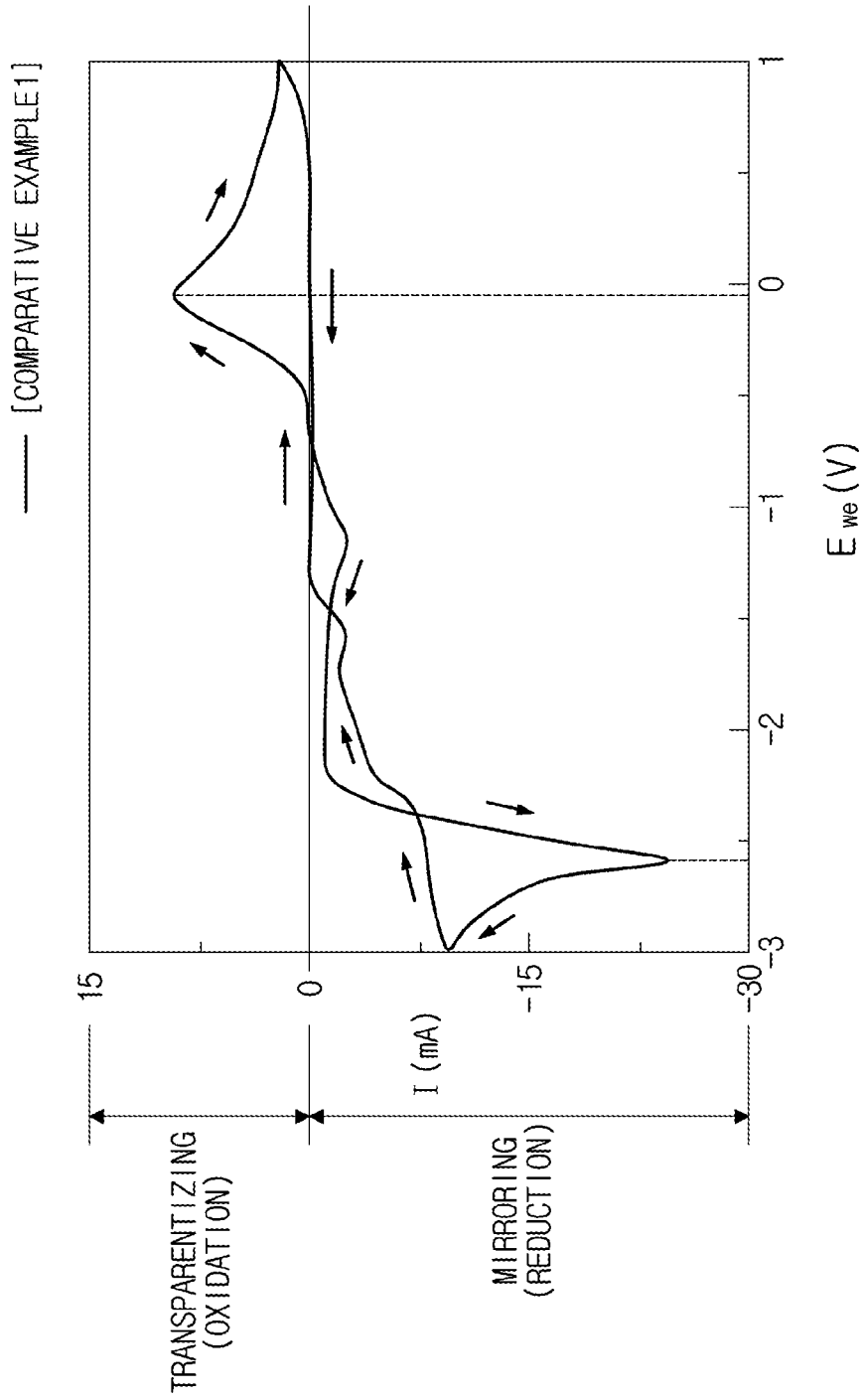
FIG. 10 illustrates CV curves of the electrolyte solution according to Comparative Example 1.

FIGS. 7 to 10 are graphs illustrating cyclic voltammogram (CV) curves obtained by measuring electrochemical redox behavior of the electrolyte solutions. More particularly, FIG. 7 illustrates CV curves of the electrolyte solution according to Example 1. FIG. 8 illustrates CV curves of the electrolyte solution according to Example 2. FIG. 9 illustrates CV curves of the electrolyte solution according to Example 3. FIG. 10 illustrates CV curves of the electrolyte solution according to Comparative Example 1.

FIGS. 7 to 10 illustrate electrochemical redox behavior of the electrolyte solutions according to Examples 1, 2, and 3 and Comparative Example 1 under the conditions of 20 mV/sec, a voltage of −3 V to 1 V, and 100 cycles.

Referring to CV curves of Examples 1, 2, and 3 illustrated in FIGS. 7 to 9, it was confirmed that first peaks were observed in a reduction region of about −1.8 V to −0.7 V and second peaks were observed in a reduction region of about −3 V to −2.2 V. It was also confirmed that no peaks were observed in an oxidation region of about −0.5 V to 1 V.

Referring to FIG. 7, in the case of the electrolyte solution according to Example 1, a first peak was observed at a reduction region of about −1.5 V, a second peak was observed at a reduction region of about −2.8 V, and no peak was observed in an oxidation region of −0.5 V to 1 V.

Referring to FIG. 8, in the case of the electrolyte solution according to Example 2, a first peak was observed at a reduction region of about −1.3 V, a second peak was observed at a reduction region of about −2.5 V, and no peak was observed in an oxidation region of −0.5 V to 1 V.

Referring to FIG. 9, in the case of the electrolyte solution according to Example 3, a first peak was observed at a reduction region of about −1.4 V, a second peak was observed at a reduction region of about −2.8 V, and no peak was observed in an oxidation region of −0.5 V to 1 V.

In the case of the electrolyte solution according to Comparative Example 1 illustrated in FIG. 10, a first peak was observed at a reduction region of about −2.6 V, and a second peak was observed at an oxidation region of about 0 V. No peak was observed in a reduction region of −1.8 V to −0.7 V.

Based on the test results, it was confirmed that the first peaks were observed at a reduction region of about −1.8 V to −0.7 V in the case of the electrolyte solutions according to Examples 1 and 2 including the 1,3-propanesultone additive that is a different electrolyte solution from that of Comparative Example 1 which did not include the 1,3-propanesultone additive. Thus, it may be deduced that the peak observed at the reduction region of about −1.8 V to −0.7 V was obtained by 1,3-propanesultone.

Next, it was confirmed that a peak similar to that of Comparative Example 1 was observed at the reduction region of about −3 V to −2.2 V. Thus, it was confirmed that the peak observed at the reduction region of about −3V to −2.2 V indicates mirroring reduction behavior by which nucleation and growth of silver (Ag) are progressed.

It was confirmed that 1,3-propanesultone additive serves as a catalyst inducing rapid mirroring during a reduction process from silver ions ($Ag^+$) to silver metal particles (Ag) based on the CV results.

Regarding the transparentizing speed, a peak was observed at an oxidation region of −0.5 V to 1 V in the case of the electrolyte according to Comparative Example 1, which did not include 1,3-propanesultone additive. Accordingly, it was confirmed that a relatively large current is required to dissociate metal particles constituting the electrochemical mirror layer 150, and the electrochemical mirror, which did not include 1,3-propanesultone additive, had a relatively low transparentizing speed.

On the contrary, no peak was observed in an oxidation region of −0.5 V to 1 V in the electrolyte solutions according to Examples 1 and 2 including the 1,3-propanesultone additive. Thus, it was confirmed that an electrochemical mirror having a high switching speed even in a low current may be provided by using the 1,3-propanesultone additive.

Since the electrolyte solution according to Example 3 exhibited similar behavior to the electrolyte solutions according to Examples 1 and 2, it may be deduced that the linear sulfonate compound serves as a catalyst inducing rapid mirroring. It was confirmed that an electrochemical mirror having a high switching speed may also be provided by using the linear sulfonate compound in the same manner as in the case of using the cyclic sulfonate compound.

As apparent from the above description, according to the electrochemical mirror according to exemplary embodiments, the following effects may be achieved:

First, an electrochemical mirror having high electrochemical stability and excellent cycle characteristics may be provided by using only a process of adding the sulfonate additive to the electrolyte solution.

In addition, an electrochemical mirror that is rapidly switchable between light-reflecting and light-transmitting modes may be provided by reducing internal resistance of the cell.

According to exemplary embodiments, mirroring (reduction) and transparentizing (oxidation) may be reversibly realized, and thus switching mirrors may be implemented by using a relatively simple process.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electrochemical mirror comprising:
a first transparent electrode;
a second transparent electrode disposed to be spaced apart from the first transparent electrode; and
an electrolyte layer disposed between the first transparent electrode and the second transparent electrode and comprising an electrolyte solution, the electrolyte solution comprising a sulfonate compound having a sulfonate functional group or a derivative compound having the sulfonate functional group, as an electrolyte solution additive.

2. The electrochemical mirror according to claim 1, wherein the sulfonate compound has at least one among a cyclic form and a linear form.

3. The electrochemical mirror according to claim 2, wherein the sulfonate compound has the cyclic form which is represented by a Structural Formula 1:

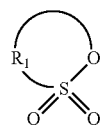

wherein, in the Structural Formula 1, an $R_1$ group includes a hydrogen or one of an alkyl group, an alkene group, or an alkyne group having 1 to 10 carbon atoms, respectively.

4. The electrochemical mirror according to claim 3, wherein, in the one of the alkyl group, the alkene group, or the alkyne group, one of hydrogen atoms is substituted with the sulfonate compound, respectively.

5. The electrochemical mirror according to claim 3, wherein the Structural Formula 1 comprises more than one $R_1$ group.

6. The electrochemical mirror according to claim 3, wherein the Structural Formula 1 comprises an ether group in at least one among a ring and the $R_1$ group.

7. The electrochemical mirror according to claim 2, wherein the sulfonate compound has the linear form which is represented by a Structural Formula 2:

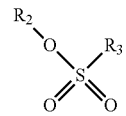

wherein, in the Structural Formula 2, each of an $R_2$ group and $R_3$ group is hydrogen or one of an alkyl group, an alkene group, or an alkyne group having 1 to 10 carbon atoms, respectively.

8. The electrochemical mirror according to claim 7, wherein, in the one of the alkyl group, the alkene group, or the alkyne group, one of hydrogen atoms is substituted with the sulfonate compound, respectively.

9. The electrochemical mirror according to claim 7, wherein at least one among the $R_2$ group and the $R_3$ group of the Structural Formula 2 comprises an ether group.

10. The electrochemical mirror according to claim 9, wherein the electrolyte solution comprises at least one material selected from an ammonium bromide-based material comprising tetra-n-butylammonium bromide (TBABr) or tetra-ethylammonium bromide (TEABr), a halogenated material comprising a halogenated anion and forming an organic or inorganic ionic salt with the halogenated anion, and tetra-n-butylammonium perchlorate (TBAP).

11. The electrochemical mirror according to claim 9, wherein the electrolyte solution comprises at least one solvent selected from water, dimethyl sulfoxide (DMSO), N-methyl-2-pyrrolidone (NMP), acetonitrile (AN), ethylene glycol (EG), γ-butyrolactone (GBL), dimethy formamide (DMF), a glyme-based solvent, an ether-based solvent, and a carbonate-based solvent including a linear carbonate-based solvent or a cyclic carbonate-based solvent.

12. The electrochemical mirror according to claim 9 wherein the electrolyte solution comprises at least one selected from polyvinyl butyral (PVB), cyano resin, polyvinylidene fluoride (PVDF), and polyvinylidene-hexafluoropropylene (PVDF-HFP), to improve viscosity and stability of the electrolyte solution.

13. The electrochemical mirror according to claim 1, wherein the sulfonate compound comprises a sulfonate compound in which multiple bonds are formed between carbon molecules.

14. The electrochemical mirror according to claim 1, wherein the electrolyte solution comprises electrodepositable metal salt ions.

15. The electrochemical mirror according to claim 14, wherein the electrodepositable metal salt ions comprise at least one selected from silver (Ag), gold (Au), magnesium (Mg), nickel (Ni), bismuth (Bi), chromium (Cr), aluminum (Al) copper (Cu), calcium (Ca), and strontium (Sr).

16. The electrochemical mirror according to claim 14, wherein, when a voltage is applied to the first transparent electrode and the second transparent electrode, the electrodepositable metal salt ions are reduced to form an electrochemical mirror layer on a surface of one among the first transparent electrode and the second transparent electrode.

17. The electrochemical mirror according to claim 1, wherein the first transparent electrode and the second transparent electrode are formed on at least one among a glass substrate, a rigid substrate, a polyethylene terephthalate (PET) substrate, and a flexible substrate.

18. An electrochemical mirror comprising:
a first transparent electrode disposed on a first substrate;
a second transparent electrode which is disposed on a second substrate and faces the first transparent electrode;
a first blocking wall and a second blocking wall which connect ends of the first transparent electrode and the second transparent electrode; and
an electrolyte layer disposed in a cavity formed between the first transparent electrode, the second transparent electrode, the first blocking wall, and the second blocking wall, the electrolyte layer comprising an electrolyte solution including electrodepositable metal salt ions and a sulfonate compound,
wherein, in response to a voltage being applied to the first transparent electrode and the second transparent electrode, the electrodepositable metal salt ions form an electrochemical mirror layer on a surface of the first transparent electrode and cause the electrochemical mirror to operate in an opaque state,
in response to stopping application of the voltage to the first transparent electrode and the second transparent electrode, the electrodepositable metal salt ions become dissociated from the surface of the first transparent electrode and cause the electrochemical mirror to operate in a transparent state, and
the sulfonate compound serves as a catalyst controlling a switching speed between the opaque state and the transparent state, of the electrochemical mirror.

19. The electrochemical mirror according to claim 18, wherein the sulfonate compound has a cyclic form which is represented by a Structural Formula 1:

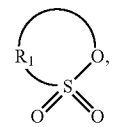

or linear form which is represented by a Structural Formula 2:

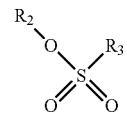

wherein, in the Structural Formula 1 and the Structural Formula 2, each of an $R_1$ group, an $R_2$ group, and an $R_3$ group includes a hydrogen or one of an alkyl group, an alkene group, or an alkyne group having 1 to 10 carbon atoms, respectively.

20. The electrochemical mirror according to claim 19, wherein, in the one of the alkyl group, the alkene group, or the alkyne group, one of hydrogen atoms is substituted with the sulfonate compound, respectively.

* * * * *